(12) United States Patent
Geier et al.

(10) Patent No.: US 7,771,712 B2
(45) Date of Patent: Aug. 10, 2010

(54) COMPOSITION FOR ATTRACTING BLOOD SUCKING ARTHROPODS AND FRUIT FLIES

(76) Inventors: Martin Geier, Cart-Maria-Von-Weber-Strasse 7g, D-93053 Regensburg (DE); Eiras Alvaro, Rua dominica 193, Itapoa, MG 31270-301 Belo Horizonte (BR)

(*) Notice: Subject to any disclaimer, the term of this patent is extended or adjusted under 35 U.S.C. 154(b) by 1013 days.

(21) Appl. No.: 10/517,675

(22) PCT Filed: Jun. 6, 2003

(86) PCT No.: PCT/EP03/05980

§ 371 (c)(1), (2), (4) Date: Jul. 20, 2005

(87) PCT Pub. No.: WO03/103395

PCT Pub. Date: Dec. 18, 2003

(65) Prior Publication Data

US 2006/0057100 A1    Mar. 16, 2006

Related U.S. Application Data

(60) Provisional application No. 60/386,582, filed on Jun. 7, 2002.

(51) Int. Cl.
A01N 25/00 (2006.01)
A61K 33/02 (2006.01)
A61K 31/19 (2006.01)

(52) U.S. Cl. .......................... 424/84; 424/719; 514/557
(58) Field of Classification Search .................. 424/84, 424/719; 514/557
See application file for complete search history.

(56) References Cited

U.S. PATENT DOCUMENTS 5,907,923 A * 6/1999 Heath et al. .................... 43/122
2002/0028191 A1 * 3/2002 Bernier et al. ................. 424/84

OTHER PUBLICATIONS

Bosch et al, Chem. Senses, 2000, 25, 323-330.*

* cited by examiner

Primary Examiner—Johann R Richter
Assistant Examiner—Abigail Fisher
(74) Attorney, Agent, or Firm—Jonathon Myers; Andrew Wilford

(57) ABSTRACT

The present invention is directed to a composition for attracting blood sucking arthropods and fruit flies. Furthermore, the present invention is directed to a method of attracting blood sucking arthropods and fruit flies and to a kit or trap, comprising the components of said composition.

5 Claims, 5 Drawing Sheets

Experimental device

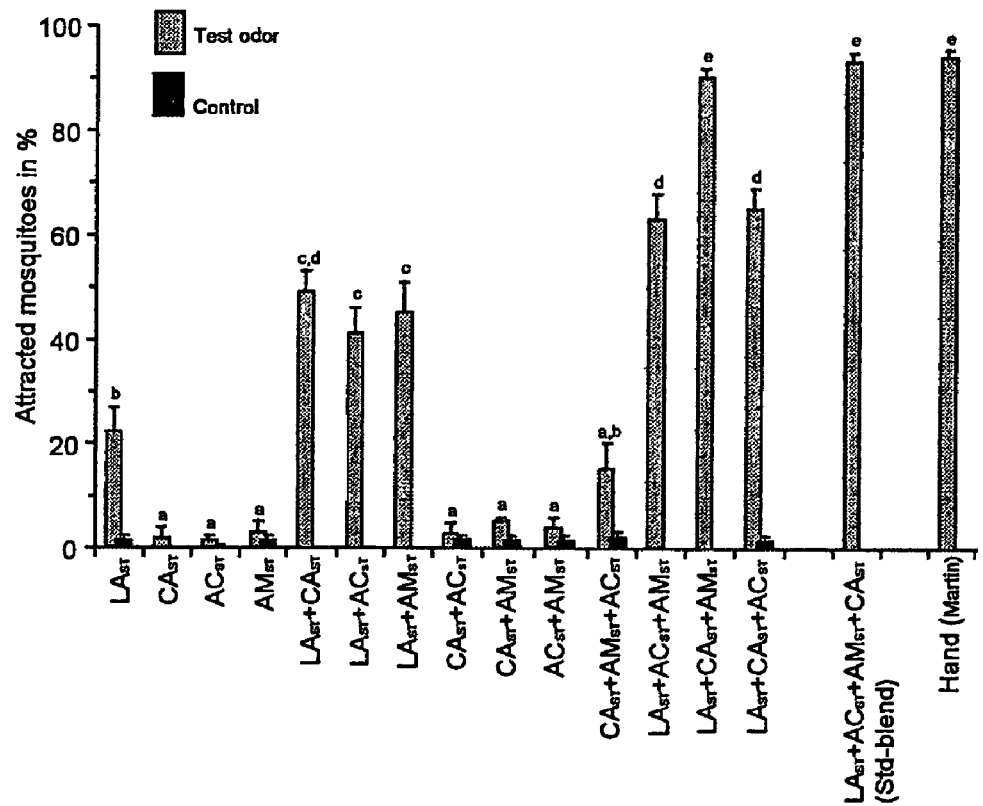
Fig. 1. Responses of female *A. aegypti* to different combinations of four components of human body odor.

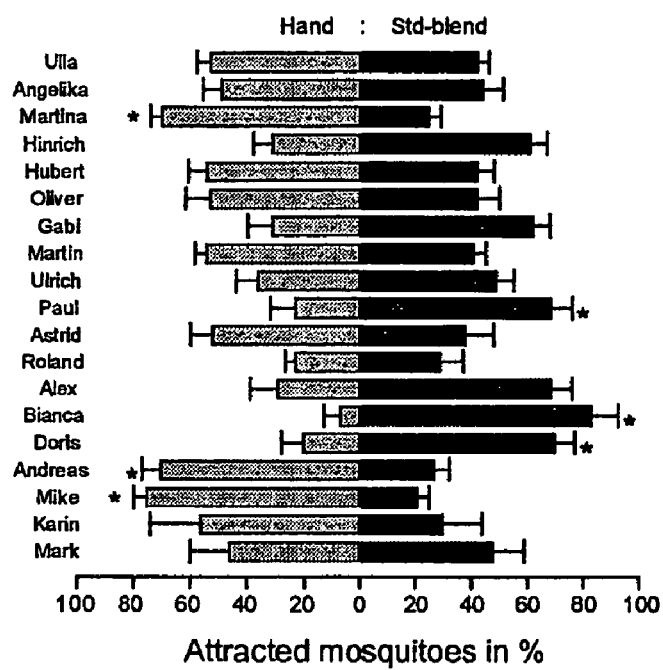
Fig. 2. Mosquitoes' choice between the human hand and the standard blend.

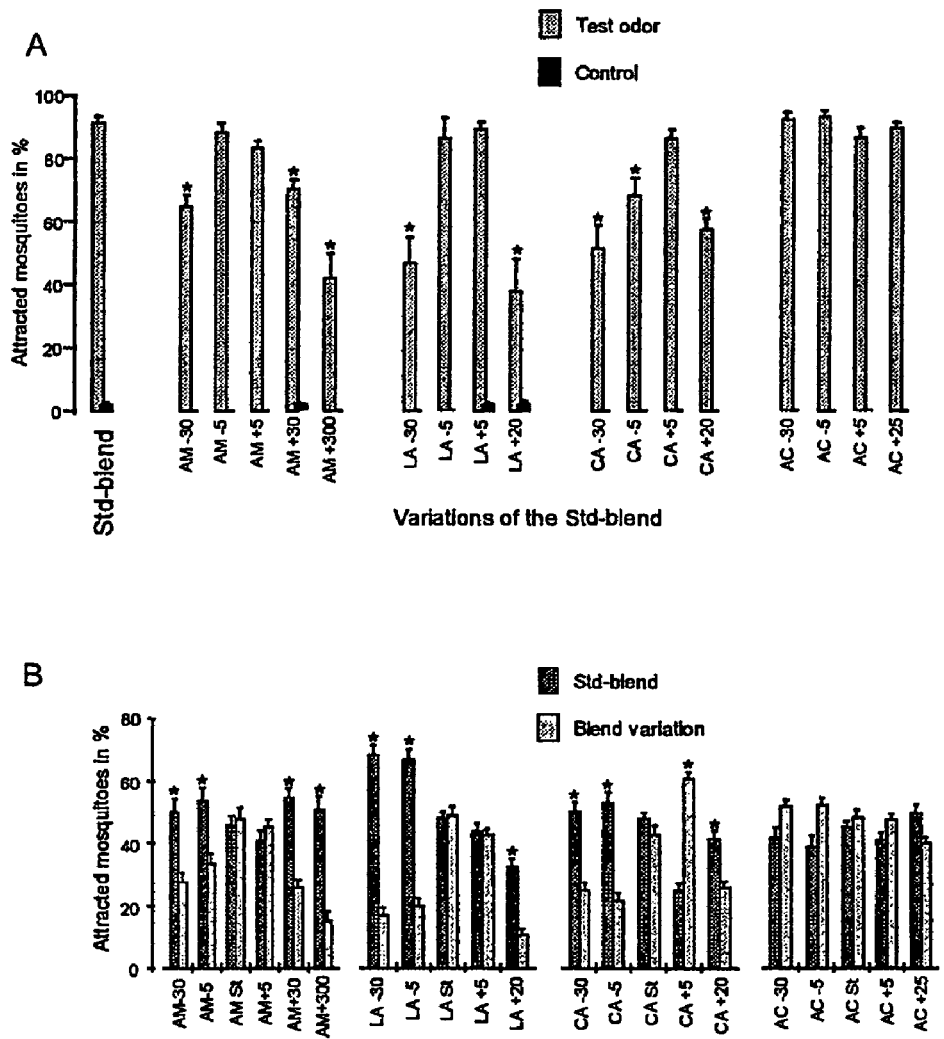
Fig. 3. Behavioral responses to varying proportions of each component in the synthetic blend.

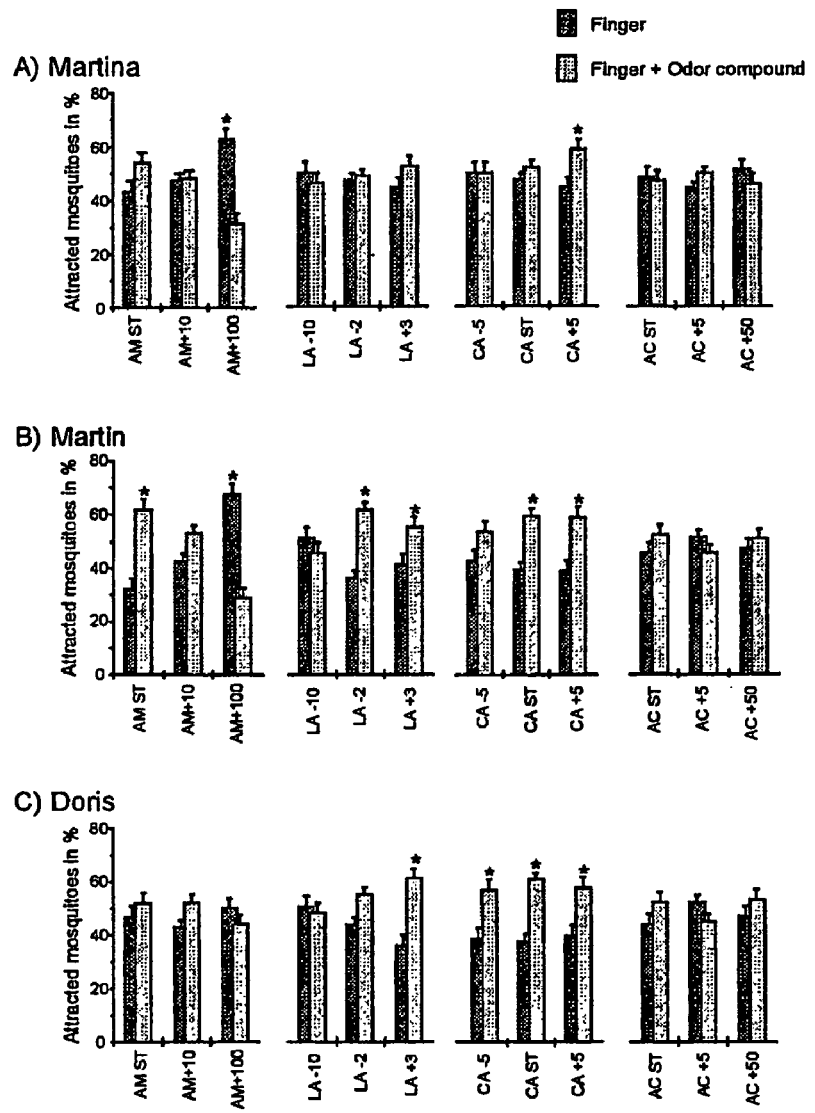
Fig. 4. Behavioral effect of adding synthetic odor compound to natural blends of humans

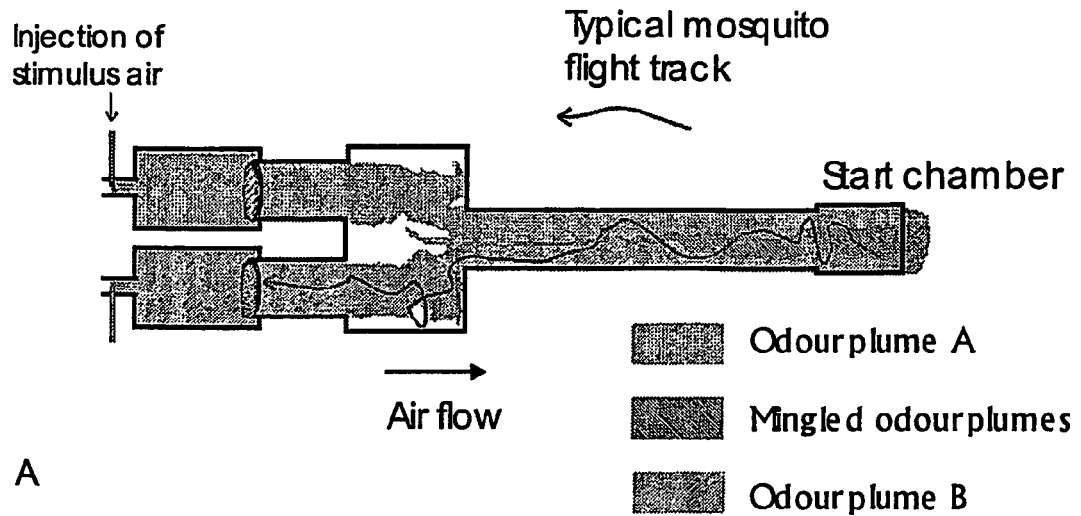
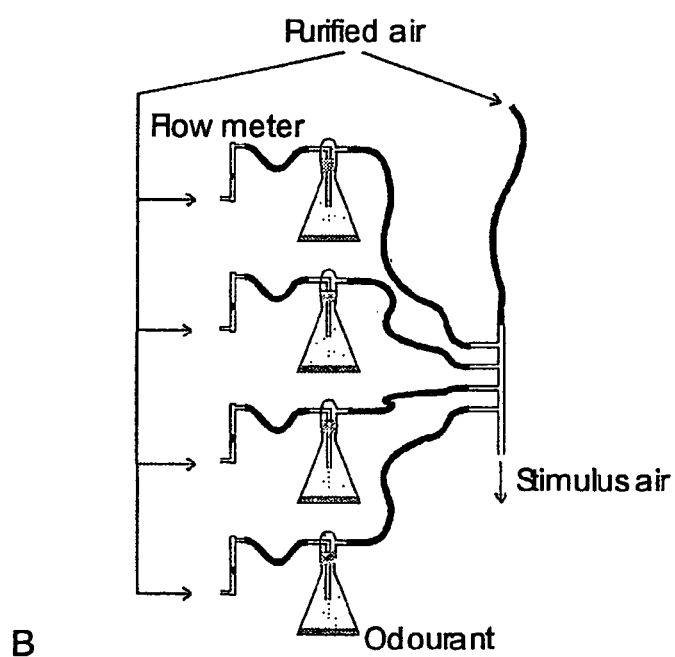
Fig.5: Experimental device

COMPOSITION FOR ATTRACTING BLOOD SUCKING ARTHROPODS AND FRUIT FLIES

CROSS REFERENCE TO RELATED APPLICATIONS

This application is the US national phase of PCT application PCT/EP03/05980, filed 6 Jun. 2003, published 18 Dec. 2003 WO 03/103395, and claiming the priority of U.S. provisional application 60/386,582 filed 7 Jun. 2002.

FIELD OF THE INVENTION

The present invention is directed to a composition for attracting blood sucking arthropods and/or fruit flies. Furthermore, the present invention is directed to a method of attracting blood sucking arthropods and to a kit or trap, comprising the components of said composition.

STATE OF THE ART

Olfactory cues are widely used by blood sucking insects to detect and to find sources for blood meals. Since blood sucking arthropods are one of the most important groups of vectors for human and animal disease, many attempts have been undertaken to explore the attractive blend of host odours. For example, different mosquito species have developed different host preferences and it is generally assumed that host selection and discrimination is mainly based on olfactory cues. One important kairomone is $CO_2$, a major component of breath that has been shown to activate and to attract a number of blood sucking insect species (Gellees 1980; Takken 1991; Eiras and Japsen 1994; Geier et al. 1999). Another is L-(+)-lactic acid, a component present in human breath as well as on human skin. This compound is only slightly effective by itself, but acts synergistically with $CO_2$ and other components from human skin, at least for the Yellow Fever Mosquito *Aedes aegypti* (Geier et al., 1996). Interestingly, the latter components were found to be attractive only in combination with lactic acid.

Carbon dioxide has been shown to attract mosquitoes. Willis, J. Exp. Zool, 121, 149-179 (1952), discloses that *Aedes aegypti* are attracted to carbon dioxide. The role of carbon dioxide in the attraction of mosquitoes to hosts also has been the subject of numerous laboratory studies. Rudolfs, N. J. Agric. Exp. Sta. Bull., 367 (1922), and Gouck, J. Econ. Entomol., 55, 386-392 (1962), describe carbon dioxide as an activator, rather than an actual attractant. However, it is noted that carbon dioxide itself, i.e. as a single compound, is less attractive as the natural host, e.g. human host. Therefore, it may not be serve as a powerful attractant alone.

Acree, et al., Science 161, 1346-7 (1968), disclose that L-lactic acid, isolated from the human hand, attracts female *Aedes aegypti*. It is also disclosed that carbon dioxide is necessary to observe this attraction.

Wensler, Can. J. Zool., 50, 415-420 (1972), discloses the use of ethyl ether soluble honey odors to attract *A. aegypti*.

Compositions consisting of lactic acid analogues and carbon dioxide have also been shown to attract mosquitoes. Carlson, J. Econ. Entomol., 66, 329-331 (1973), discloses that some tested analogues of lactic acid had equivalent attraction to L-lactic acid, but this was not true at all tested doses. The highest reported attraction was 40% of female *A. aegypti*.

Bar-Zeev et al., J. Med. Entomol., 14, 113-20 (1977), disclose that a composition consisting solely of lactic acid and carbon dioxide attracts *A. aegypti*. Here, the lactic acid was dissolved in acetone Price, J. Chem. Ecol., 5, 383-95 (1979), discloses that human emanations and carbon dioxide attract female *Anopheles quadrimaculatus*.

Gillies, Bull. Entomol. Res., 70, 525-32 (1980), reviews the use of carbon dioxide to activate and attract mosquitoes. The drawbacks in the use of carbon dioxide alone as an attractant for blood sucking arthropods are as explained above.

Schreck, J. Chem. Ecol., 8, 429-38 (1981), discloses that materials isolated from human hands, other than L-lactic acid, attract female *A. aegypti* and, *A. quadrimaculatus* mosquitoes.

Lactic acid, in combination with phosphorous-containing compounds have been shown to attract mosquitoes. Ikeshoji, Jpn. J. Sanit Zool., 38, 333-38 (1987), discloses lactic acid and hempa; lactic acid and metepa; lactic acid, metepa and olive oil; and lactic acid and DDVP attract mosquitoes.

Lactic acid-related compounds have also been tested as mosquito attractants by electrophysiology. Davis, J. Insect Physiol., 34, 44349 (1988), discloses that neurons in the antennae are excited by L-lactic acid, and that analogues of lactic acid, e.g., carboxylic acids, alcohols, hydroxyacids, aldehydes, thiols and haloacids were tested for neuron response. It was shown that no compound elicited as high of a relative responsiveness toward lactic acid-excited cells as did lactic itself. Lactic acid was shown to excite neurons in the antennae of virgin *A. aegypti* by Davis, J. Insect Physiol., 30, 211-15 (1984). It has been shown that carbon dioxide, in combination with other chemicals, serves as an attractant for mosquitoes. Takken and Kline, J. Am. Mosq. Control Assoc., 5, 311-6 (1989), disclose 1-octen-3-ol (octenol) and carbon dioxide as mosquito attractants. Van Essen, Med. Vet. Entomol., 63-7 (1993), discloses the use of carbon dioxide, octenol, and light to attract several species of mosquitoes. Takken, J. Insect Behavior, 10, 395-407 (1997), discloses that a composition consisting solely of carbon dioxide, acetone and octenol attracts several species of mosquitoes.

Kline, Med. Vet. Entomol., 4, 383-91 (1990), discloses that honey extract, octenol, carbon dioxide, L-lactic acid plus carbon dioxide, L-lactic acid plus octenol plus carbon dioxide attract mosquitoes well and butanone plus carbon dioxide, and phenol alone are less effective.

Schreck, J. Am. Mosq, Control Assoc., 6, 406-10 (1990), discloses that materials isolated from human skin attract female *A. aegypti* and *A. quadrimaculatus*, and that the level of attraction, varies from person to person. It is also disclosed that differences in attraction level are present depending on the body location origin of the material.

Takken, Insect Sci. Applic., 12, 287-95 (1991), reviews mosquito attractants and lists acids, alone or in combination with other amino acids that are attractive for mosquitoes.

Eiras, Bull. Entomol. Res., 81, 151-60 (1991), discloses that lactic acid, carbon dioxide, human sweat and thermal convection currents attract female *A. aegypti*.

Carlson, J. Med. Entomol., 29, 165-70 (1992), discloses that the release of carbon dioxide from the human hand is negligible and therefore is not a factor in the attraction of *A. aegypti* to the human hand.

Bowen, J. Insect Physiol., 40, 611-15 (1994), discloses that lactic acid sensitive receptors are present in *Ae. atropalpus*.

Eiras, Bull. Entomol. Res., 81, 207-11 (1994), discloses that lactic acid in combination with carbon dioxide has been shown to attract mosquitoes.

Charlwood, *Ann. Trop. Med. Parasitol.*, 89, 327-9 (1995), discloses the mosquito-mediated attraction of female mosquitoes to hosts. Several species of mosquitoes were more attracted to a host, e.g., human leg, which already had mosquitoes feeding than a host which had no mosquitoes feeding on the host (termed "invitation effect"). An apparent pheromone, which was given off by the feeding mosquitoes, was speculated to attract other mosquitoes to the host.

DeJong and Knols, Experientia, 51, 80-4 (1995), discloses that different malaria mosquito species (*An. gambiae* s.s. and *An. atroparvus*) prefer different biting sites on the human body. DeJong and Knols, Acta Tropica, 59, 333-5 (1995), disclose that *An. gambiae* is attracted to carbon dioxide.

Bernier, Ph.D. Dissertation, University of Florida (1995), discloses the presence of lactic acid, glycerol, and long chain acids and alcohols on the skin, as well as other chemicals for a total of over 300 compounds. Some of these were identified and examined as candidate attractants.

Geier, in *Olfaction in Mosquito-Host Interactions*, 13247 (1996), discloses that carbon dioxide alone is an attractant and that lactic acid alone is a mild attractant, but that the two act as a synergistic attractant. It also discloses that fractions of ethanol washings from human skin are attractive.

McCall, J. Med. Entomol., 33, 177-9 (1996), discloses that *A. aegypti* were attracted to volatile constituents of mouse odor, but did not identify potential chemicals.

Knols, Bull. Entomol. Res., 87, 151-9 (1997), discloses the use of Limburger cheese (the acid and non-acid solvent extracted fractions) to attract *An. gambiae*. Nineteen saturated and unsaturated aliphatic fatty acids, ranging in carbon chain lengths from C2-C18 were identified in Limburger cheese.

Mboera, J. Vector Ecol., 23, 107-13 (1998), disclosed that *Culex quinquefasciatus* is attracted to a worn stocking and that carbon dioxide plus body odor did not increase response.

Kline, J. Vector. Ecol., 23, 186-94 (1998), disclosed that in olfactometer tests, the human hand or worn sock attracted 80% and 66%, respecively, of *A. aegypti* in the cage. In comparison, Limburger cheese attracted 6.4%, and the control 0.0% in the olfactometer.

Bernier, Anal, Chem., 71, 1-7 (1999), discloses the method for analysis of skin emanations, including the identification of lactic acid, glycerol, C12-C18 carboxylic acids and C4-C11 aldehydes.

Geier and Boekh, Ent. Exp. et Appl., 92: 9-19, 1999 describe the response of mosquitoes to host odors, e.g. lactic caid and carbon dioxide in a small Y-shaped wind tunnel.

Geier et al., Chem. Senses 24: 647-653, 1999, describe lactic acid as an essential synergist for ammonia as an attractant for *Aedes aegypti*.

Takken and Knots, Annu. Rev. Entomol., 44, 131-57 (1999), reviewed odor-mediated behavior of afrotropical mosquitoes, reaffirming carbon dioxide as the best known mosquito kairomone.

Braks and Takken, J. Chem. Ecol., 25, 663-72 (1999), disclose that 2-day-old incubated sweat became attractive to *An. gambiae*.

Geier et al., Chem. Senses 25: 323-330, 2000, describe the attractive effect of mixtures containing ammonia, lactic acid plus two fatty acids.

Various chemicals have been disclosed as attractants for mosquitoes. U.S. Pat. No. 4,818,526 to Wilson discloses the use of dimethyl disulfide and dibutyl succinate and combinations thereof as attractants for *Culicidae* (mosquitoes).

U.S. Pat. No. 4,907,366 to Balfour (1990) discloses the use of a composition consisting solely of lactic acid, carbon dioxide, water, and heat to attract mosquitoes.

PCT WO 98/26661 to Justus discloses mixtures of L-lactic acid and its sodium salt, glycerol, and cheese extracts, with and without unsaturated long chain carboxylic acids, alcohols and an amide as attractive for *A. aegypti*. The glycerol, as well as other components described as equivalent to the glycerol, appear to make the composition substantive, so that it does not evaporate immediately in a rapid pulse. However, the active ingredients from Limburger cheese, which are the attractant chemicals, are not disclosed within the document, nor were statistical data reported for the results used in the examples.

U.S. Pat. No. 6,267,953 B1 to Bernier (2001) discloses the use of a composition consisting of lactic acid, aceton, and dimethyl disulfid to attract mosquitoes.

Several of the above-mentioned chemicals and chemical compositions have been employed to attract any of the hundreds of species of mosquitoes and related arthropods that utilize humans and animals as their hosts. In fact, many of the disclosed compositions have been claimed to be active as attractants for mosquitoes. However, the activities of these attractants are often inconsistent and below 50% attraction response in laboratory experiments. Furthermore, none of the disclosed compositions have been shown to be able to attract mosquitoes on a consistent basis as efficiently as, or more efficiently than the human body. Moreover, synthetic chemicals that are unsafe for the environment or that may be dangerous to human health have been used in some of the known compositions.

Therefore, it is the object of the present invention to provide chemical compositions that can be employed safely in the environment, and that exhibit a synergistic effect for attracting mosquitoes and fruit flies wherein the compositions are as efficient than the human body or more efficient in attracting mosquitoes and at least as sufficient or more efficient in attracting fruit flies than fruit.

These objects are solved by the subject-matters of the independent claims. Preferred embodiments are set forth in the dependent claims.

SUMMARY OF THE INVENTION

The present inventors surprisingly found that a certain mixture of components is more attractive to blood sucking arthropods and fruit flies than the single components or the same components in binary mixtures. Unexpectedly, it further turned out that a crucial parameter for attractiveness is the mixing ratio of said components in the gaseous phase. Compositions comprising the same ingredients could be observed as being unattractive when leaving a certain range of mixing ratios in the gaseous phase. The mixing ratio in the gaseous phase could also be defined as that part of the composition, which is directly perceptible by the arthropods' sense organs.

The term "mixing ratio in gaseous phase" as used herein is to be understood as the molar amount and mixing ratio of gaseous components. These components may be provided in liquid, solid, or gaseous form. When provided as liquids or solids, they may be allowed to evaporate in order to provide the gaseous form of a component. Upon mixing and/or diffusion, the molar ratio of the compounds relative to each other in the gaseous phase is defined as "mixing ratio in the gaseous phase". The amount of a given compound that is evaporated is termed the "evaporated amount". For the purposes of this application, this term shall also include amounts of compounds provided in the gaseous phase, which have not evaporated. The amount referred to is the amount of the compound in the gaseous space where all of the compounds of the inventive composition are mixed together.

The compositions disclosed herein are provided to attract blood sucking arthropods and fruit flies. Both "blood sucking arthropod" and "fruit fly" are members of the phylum Arthropoda, which is the largest phylum in the animal kingdom, comprising about 75% of all animals that have been described. The estimated number of arthropod species is between 1.000.000 and 2.000.000. Arthropods vary in size from the microscopic mites to the giant decapod crustaceans.

The phylum Arthropoda includes many families of insects that are of a medical and veterinary importance, e.g., mosquitoes (Culicidae), blackflies (Simuliidae), sand flies (Phlebotominae), biting midges (Ceratopogonidae), horseflies (Tabanidae), tsetse flies (Glossinidae), stable flies and house flies (Muscidae), fleas (Siphonaptera), lice (Anoplura), triatomine bugs (Triatominae), soft ticks (Argasidae) and hard ticks (Ixodidae).

Preferred blood sucking arthropods include mosquito (Culicidae), blackfly (Simuliidae), sand fly (Phlebotominae), biting midge (Ceratopogonidae), horsefly (Tabanidae), tsetse fly (Glossinidae), stable fly and house fly (Muscidae), flea (*Siphonaptera*), louse (Anoplura), triatomine bug (Triatominae), soft tick (Argasidae) and hard tick (Ixodidae).

It is appreciated that "mosquito" can be any of the mosquitoes belonging to the suborder diptera known as Nematocera. This suborder includes the family Culicidae. The 3400 or so species of mosquitoes are arranged in 38 genera. The Culicidae are divided into three subfamilies: the Anophelinae, including the well-known genus *Anopheles*, many species of which are responsible for the transmission of malaria; the Toxorhynchitinae, the large larvae of which eat other mosquito larva; and the Culicinae which, with about 2930 species in about 34 genera, are divided into two tribes: the Culicini and the Sabethini. The Culcine mosquitoes include such well known genera as *Culex, Aedes* and *Mansonia*. The sebethene mosquitoes include *Sabethes, Wyeomyia* and *Malaya*. A specific mosquito is one belonging to one of the genera *Culex, Aedes, Psorophora, Wyeomyia, Mansonia, Coquilletidia* and *Anopheles*.

A preferred blood-sucking arthropod is a mosquito belonging to the genera *Culex, Aedes, Mansonia, Wyeomyia, Psorophora, Coquilletidia* or *Anopheles*. Further preferred blood-sucking arthropods include Simulidae, Triatoninae, Siphonaptera, Tabanidae, Culicoides, Phleobotomines, Muscidae, Glossinidae, Ixodidae or Argasidae.

Further included are, of the subfamily Phlebotominae (sandflies) (i.e. Order: Diptera; Suborder: Nematocera; Infraorder: Psychodomorpha; Superfamily: Psychodoidea; Family: Psychodidae), the Genus: *Lutzomyia* and Genus *Phlebotomus*.

Regarding fruit flies, included are all species of *Drosophila*.

The composition for attracting blood sucking arthropods and/or fruit flies according to the invention comprises an effective amount of the following:
a) at least one compound from group I, III or III or an acceptable salt thereof or a combination thereof with
  group I consisting of alpha-hydroxycarboxylic acids, particularly alpha-hydroxymonocarboxylic acids, each containing a $C_0$-$C_8$ alkyl chain group,
  group II consisting of alpha-thiomonocarboxylic acids and alpha-thiodicarboxylic acids, each containing a $C_0$-$C_8$ alkyl chain group,
  group III consisting of at least one compound of group I or II wherein the alkyl group is substituted by a $C_6$-$C_{10}$ aryl group;
b) at least one compound which is a $C_4$-$C_8$ carboxylic acid or an acceptable salt thereof, selected from the group consisting of butyric acid, valeric acid, caproic acid, oenanthic acid, caprylic acid and variations thereof, wherein said variations are defined as having one or more unsaturated bonds and/or being branched carboxylic acids;
c) ammonia and/or primary amines with $C_1$-$C_6$ atoms.

The term primary amine as used herein encompasses all derivatives of ammonia, in which one hydrogen atom has been substituted by an alkyl chain of from 1-6 C-atoms.

According to a preferred embodiment, the alkyl chains (group I and/or II) contain 1, 2, 3, 4, 5, 6, 7 or 8 carbon atoms. It is further preferred that the aryl group of group III is a phenyl group.

Compound a) is preferably selected from glycolic acid, thiolactic acid, lactic acid, thiomalic acid, tartaric acid and/or mandelic acid. It is noted that the composition according to the present invention is not restricted to the use of only one of the compounds of group I, II and III mentioned in feature a), above. It is also comprised by the scope of the present invention to use two or more of those components, if they show or contribute to synergistic effects as attractants for blood sucking arthropods or fruit flies.

Instead of caproic acid, heptanoic acid can be preferably used as heptanoic acid is free of antidesired smell. In another embodiment, heptanoic acid is used additionally to caproic acid.

Instead of ammonia, ammonia-releasing compounds can be used. Examples are $(NH_4)_2CO_3$ (ammonium carbonate), $NH_4HCO_3$ (ammonium hydrogen carbonate), $(NH_4COONH)$ (ammonium carbamate, $NH_4Cl$ (ammonium chloride) and other ammonia salts.

Examples for compounds of group I are glycolic acid, lactic acid, tartaric acid.

Examples for compounds of group II are thiolactic acid and thiomalic acid.

An example for a compound of group III is mandelic acid.

Examples for primary amines are ethylamine, propylamine, butylamine and pentylamine.

An example for a branched carboxylic acid of component b) is isovaleric acid or isobutyric acid.

According to a preferred aspect, the present invention provides a composition comprising lactic acid, caproic acid, ammonia, and/or acceptable salts thereof.

As mentioned above, an important parameter for the present compositions in view of their characteristics as attractant for blood sucking arthropods is the mixing ratio in the gaseous phase.

According to one aspect of the invention, in the composition for attracting arthropods, the components a:b:c are present in a molar amount of about 1:0.1-100:0.01-10 or 1:0.5-50:0.05-5 or 1:1-10:0.1-1 with respect to their mixing ratio in gaseous phase.

According to a preferred embodiment of the invention the components a:b:c are present in a molar amount of about 1:1:0.6 with respect to their mixing ratio in gaseous phase.

The compositions for attracting arthropods may further comprise as component d one or more of further blood sucking arthropod attracting compounds, which preferably are selected from the group of at least one of $C_1$-$C_3$ carboxylic acids and acceptable salts thereof. Those may be selected from the group consisting of formic acid, acetic acid and propionic acid and at least one of dichlormethane, trichlormethane, acetone, phenol, 1-octen-3-ol, fermenting yeast, and an extract of fermenting yeast. An especially preferred component d is acetic acid.

A further preferred composition is one wherein component d comprises at least one of formic acid, acetic acid, or propionic acid.

The compositions which comprise one or more of components d, preferably comprise components a:b:c:d in a molar amount of about 1:0.1-100:0.01-10:0.01-1000 further preferably about 1:0.1-100:0.01-10:0.01-100, more preferably about 1:0.1-100:0.01-10:0.01-50 further preferably about 1:1-10:0.1-1:0.1-1 more preferably about 1:1-2:0.2-0.8:0.1-0.3 with respect to their mixing ratio in gaseous phase.

A preferred composition, comprising components a, b, c and d comprises an effective amount of lactic acid, ammonia, caproic acid, acetic acid or acceptable salts thereof. The compounds are preferably present in the ratios given above, most preferably in a molar amount of about 1:1:0.6:0.2 with respect to their mixing ratio in gaseous phase.

According to a preferred embodiment, ammonia is included in a mixing amount of not more than 10 times compared to lactic acid with respect to their mixing ratio in gaseous phase.

Preferably, the mixing ratio of lactic acid and caproic acid is between 10:1 and 1:10 with respect to their mixing ratio in gaseous phase.

If the compositions of the present invention contain ammonia and lactic acid, the mixing ratio of ammonia and lactic acid preferably is between 1:1 and 1:50 with respect to their mixing ratio in gaseous phase.

If the compositions of the present invention contain acetic acid and lactic acid, the mixing ratio of acetic acid and lactic acid is between 1:1 and 1:100 with respect to their mixing ratio in gaseous phase.

Preferably, the amount of caproic acid is higher than the mixing amount of lactic acid and the amount of ammonia is lower than the amount of lactic acid in the gaseous phase.

It should be emphasized that the compositions of the present invention are not restricted in quality or quantity to the above mentioned components and their effects, but may additionally contain further ingredients like stabilizers, fragrances, preservatives, diluting agents. Also, the compositions may additionally comprise other attractants for arthropods, such as an effective amount of carbon dioxide. Furthermore the effects of the compositions disclosed herein may be further enhanced by combining them with other attractants, e.g. visual stimuli, heat, moisture and wind.

The present invention is further directed to traps or kits, which contain the above mentioned components. Preferably, those traps or kits comprise containers or vials, wherein components a, b, c and d (if present) preferably each are located in separated containers or vials. The quantity of the components a, b, c and d is selected to provide an effective mixing ratio in the gaseous phase (as disclosed above) in a respective environment (dependent on ambient temperature, moisture and the like).

To effectively control the evaporating amount of components a, b, c and d, the trap or kit may further comprise means for controlled release of components a, b, c and d.

The compositions of the present invention may be added in any form, to a commercial or home-made trap to enhance the collection of the arthropod. The composition may diffuse out or away from the trap with or without a gas stream (e.g., air, carbon dioxide, etc.) as a carrier.

As used herein, a trap is a device that ensnares an arthropod. Effective traps include those well known in the art. Suitable traps are commercially available from different sources (e.g., Mosquito Magnet™, available from American Biophysics, Corp., 2240 South County Trail, East Greenwich, R.I. 02818-1536, USA., Mosquito Trap MK01 by Lentek, and The Mosquito Trap U.S.A., both available from Comfort House, 189-V Frelinghuysen Ave., Newark, N.J. 07114-1595

The compositions of the present invention may be delivered in vials or other sample containers. The compositions may be blended together in one single vial or container, or can be located in separate vials or containers, the latter being preferred (see above).

The compositions of the present invention may be delivered in the gas phase, such as by a compressed cylinder. In addition, the composition existing in the gas phase, may optionally be mixed or unmixed with an inert carrier gas.

The synergistic attractant compositions of the present invention may be provided by any number of mechanisms and in different formats appropriate to particular types of usage. The main function of the formats and mechanisms is to provide release of the attractant over a period of time sufficient to attract arthropods (e.g., mosquitoes) effectively, and especially to attract arthropods effectively to an available source of arthropod control material (e.g., insecticide, microbial agent, mechanical and electrical killing devices) which is effective against mosquitoes, and the like, as described above.

The structures used to release the attractant compositions of the present invention could be as simple as a tray carrying the composition, a housed tray or other container carrying the compositions, timed release canisters or spray cans, absorbent materials retarding the release of the attractant (e.g., fabric, paper, porous material, foam, absorbent polymer, super absorbent polymer [e.g., the super absorbent acrylic polymers as described in U.S. Pat. No. 5,679,364], containers with semipermeable membranes, vented containers, glues, and the like). The materials which would more actively attack the arthropods may be associated with the attractant (in a mixture) or may be located near the attractants so the chemicals do not adversely interact or react.

In addition, combining the compositions of the present invention with an insecticide provides a means of local extermination, not requiring wide-disbursement of the insecticide. Addition of a slow release chemical mechanism, such as paraffin, or other suitable viscous chemical (e.g., glycerol), microencapsulation techniques and all controlled release devices provide a means to reduce the evaporation rates of the compositions.

According to a further aspect, the present invention provides a method of attracting blood sucking arthropods and/or fruit flies comprising the step of exposing the environment with an evaporated composition of any one of the preceding claims, which composition is effective to attract blood sucking arthropods and/or fruit flies.

The invention also relates to a composition of matter comprising the components a, b, c and preferably d as described above and hereinbelow. The components are preferably present within said composition of matter in a ratio of molar amounts that allow said composition of matter, when placed within the means for controlled release of a device of the invention as described above and hereinbelow, to lead to the release of a composition of the invention. The means for controlled release are preferably similar to those described in example 5 and those known in the art of mosquito traps. Preferably, the molar amounts of the components in the composition of matter correspond to the molar amounts given above and hereinbelow for the composition of the invention. Preferred molar amounts are those wherein components a:b:c:d are present in a molar amount of about 1:0.1-100:0.01-10:0.01-1000. More preferred is a ratio of components a:b:c:d of 1:0.1-100:0.01-10:0.01-100. Further preferred is a ratio of components a:b:c:d of 1:0.1-100:0.01-10:0.01-100. More preferred is a ratio of components a:b:c:d of 1:0.1-100:0.01-10:0.01-50. Most preferred is a ratio of components a:b:c:d 1:1-10:0.1-1:0.1-1. All ratio numbers are given with respect to their mixing ratio in gaseous phase.

A more preferred composition of matter is one is one comprising an effective amount of lactic acid, ammonia, caproic acid, preferably, acetic acid, and/or acceptable salts thereof. A preferred ratio for this composition is one wherein the components are present in a molar amount as mentioned above. Most preferred is a ratio of about 1:1:0.6:(when acetic acid is present) 0.2 with respect to their mixing ratio in gaseous phase.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now illustrated by the following, non-limitative Examples, Drawings and description thereof. By interchanging the components as identified herein, the skilled artisan will find the best composition to attract either blood sucking arthropods or fruit flies or both. These variations and the experiments to be made are within the skill of the art.

BRIEF DESCRIPTION OF THE FIGURES

FIG. 1 shows the responses of female *A. aegypti* to different combinations of four components of human body odor, FIG. 2 shows results from a Y-tube test where mosquitoes can choose between the scent emanating from a human hand (left side) and the scent resulting from the standard blend as defined in example 1 (right side).

FIG. 3 shows behavioral responses to varying proportions of each component in the synthetic blend. A, Standard blend and blends that are modified in the concentration of only one component, B, Direct competition tests between the standard blend and the modified blends.

FIG. 4 shows the behavioral effect of adding synthetic odor compound to natural blends (index finger) of humans. A, B and C refer to different volunteers.

FIG. 5 shows the olfactometer for testing mosquitoes' odour preference. A, top view, B, arrangement for the production of various concentrations of odour

EXAMPLE 1

Measurements of attractiveness of different compositions were carried out using a Y-tube bioassay, similarly to the one described in Dekker et al., Med Vet Entomol. 16, p. 91-98, 2002. FIG. 1 shows the responses of female *A. aegypti* to different combinations of four components. Abbreviations of stimuli (dose in μmol/min): $LA_{ST}$=L-(+)-Lactic acid (0.05); $CA_{ST}$=Caproic acid (0.03); $AM_{ST}$=Ammonia (0.09); $AC_{ST}$=Acetic acid (0.02). Bars (mean±S.E.M.) represent the percentage of mosquitoes trapped in the respective upwind chamber of the olfactometer. Values from 30 trials per treatment were averaged. Treatments were tested in random order; test- and control side switched in successive tests. For statistical analysis the percentage values of the stimulus sides were compared with each other in a one-way ANOVA and LSD post-hoc tests; the letter code above the bars indicate significant differences: means with no letter in common are significantly different ($P<0.05$).

The results presented in FIG. 1 clearly show that a mixture of lactic acid, capronic acid, and ammonia, or the standard blend (lactic acid, capronic acid, ammonia and acetic acid) is similarly attractive for the mosquitoes as a human hand placed in front of the tube in the direction of the airstream.

EXAMPLE 2

Whereas in Example 1, the attractant was fed into one tube and the other tube was used as a control, the Y-tube bioassay can also be used in order to competitively compare two stimuli. In this respect, it is of interest to directly compare the compositions of the invention against the human body. FIG. 2 illustrates Mosquitoes' choice between the human hand and the standard blend. The hands of 19 Caucasian test persons were tested in direct competition against the standard blend (Std-blend) consisting of a mixture of $LA_{ST}$, $AM_{ST}$, $CA_{ST}$, and $AC_{ST}$ stimuli (labels according FIG. 1). Bars (means of 8 trials±S.E.M.) represent the percentage of mosquitoes trapped at the respective upwind chamber of the olfactometer. Asterisks indicate significant preferences ($P<0.05$; t-test for paired samples).

The results presented in FIG. 2 show that despite of variations in the relative attractiveness of the standard blend compared to the attractiveness of a hand of a volunteer in each particular case, the overall attractiveness of the standard blend compared to human volunteers, averaged over about 20 volunteers, is roughly equal or more attractive than the human body.

Thus it is possible to identify a composition according to the invention, which is a composition as described above, having an attractiveness equal or better that that of the standard blend, by measuring the said composition using a bioassay, such as the Y-tube bioassay described above. The bioassay may be carried out against a control, which is devoid of any scent, such as the assay described in example 1. The attractiveness values are then compared against those obtained using e.g., the standard blend or the human body. Alternatively, the bioassay may be carried out as described in example 2, where mosquitoes must choose between two alternative flight paths. One of the flight paths would contain the composition to be tested, whereas the other one would contain scent of the human body or of another composition, e.g., that of the standard blend. Thus, it is possible, using e.g., the competitive Y-tube bioassay, to directly compare the attractiveness of a given composition to the attractiveness of the human body or of another composition, which is preferably the standard blend described above. The compositions of the invention may therefore be tested for their activity in various ways. Preferred compositions are those that are equally attractive or more attractive, compared to the above-described standard blend. Further preferred compositions of the invention are those that are equally attractive or more attractive when compared with the body or part thereof of a human volunteer. As humans differ in their attractiveness to blood-sucking arthropods, it is preferred that the test be carried out with a number of volunteers, preferably 5 to 100, more preferably 10 to 50, most preferably about 20. The preferred blood-sucking arthropods to be used for this test are those that are described above, including mosquito (Culicidae), blackfly (Simuliidae), sand fly (Phlebotominae), biting midge (Ceratopogonidae), horsefly (Tabanidae), tsetse fly (Glossinidae), stable fly and house fly (Muscidae), flea (Siphonaptera), louse (Anoplura), triatomine bug (Triatominae), soft tick (Argasidae) and hard tick (Ixodidae). More preferred blood sucking arthropods for use in the test are mosquitoes belonging to the suborder diptera known as Nematocera, including the family Culicidae which includes the Anophelinae, including the well-known genus *Anopheles*, many species of which are responsible for the transmission of malaria; the Toxorhynchitinae, the large larvae of which eat other mosquito larva; and the Culicinae which are divided into two tribes: the Culicini and the Sabethini. Especially preferred mosquitoes are those that belong to the genera *Culex, Aedes* and *Mansonia*, furthermore *Sabethes, Wyeomyia* and *Malaya*. More preferred mosquitoes are those belonging to one of the genera *Culex, Aedes, Psorophora, Wyeomyia, Mansonia, Coquilletidia* and *Anopheles*. Most preferred is *A. quadrimaculatus* and especially, *A. aegypti*.

EXAMPLE 3

The effect of varying the proportions of each component in the attractant composition was tested using a bioassay similar to the one described in example 1 and 2. FIG. 3 shows behavioral responses to varying proportions of each component in the synthetic blend.

A) Standard blend and blends that are modified in the concentration of only one component were tested against the control stimulus. The stimulus labels indicate as to which component and concentration the blend was changed. Numbers of the stimuli labels indicate increasing or decreasing doses compared to the standard one. For example $AM_{-5}$ means a fivefold lower dose than $AM_{ST}$, $AM_{+30}$ a thirtyfold higher dose than $AM_{ST}$. Otherwise, experiments were carried out as described for FIG. 1., with 20 trials per treatment. For statistical analysis, the responses to the modified blends were compared with the responses to the standard blend in a one-way ANOVA and Dunnett LSD post-hoc tests; asterisks above the bars indicate significant ($P<0.05$) differences to the standard blend.

B) Direct competition tests between the standard blend and the modified blends. Bars (means of 20 trials±S.E.M.) represent the percentage of mosquitoes trapped in the respective upwind chamber. Dark bars represent the standard blend; white bars represent the modified blend (stimulus labels as in FIG. 3A). Asterisks indicate a significant preference ($P<0.05$, t-test for paired samples).

The results demonstrate that changes in the concentration of capronic acid, lactic acid and ammonia have a profound effect on the attractiveness of the composition. A five-fold or less increase or decrease in concentration did not have a significant influence on the attractiveness of the composition, while more extreme changes in concentration clearly lowered the attractiveness of the composition. In contrast, an up to 25-fold change in concentration of acetic acid did not significantly change the attractiveness of the composition.

When the same compositions are measured using direct competition experiments (as described in example 2), similar results are obtained (FIG. 3B).

EXAMPLE 4

In this example, the effect of adding certain compounds to the scent of a finger of a human volunteer was tested, using the set-up as described for example 1. The right and left index finger of each test person were tested in direct competition with simultaneous addition of a single compound to one finger; Martina (A) is highly, Martin (B) medium, and Doris (C) low attractive. The test components were alternately added to the right or to the left finger, respectively. Bars (means of 16 trials±S.E.M.) represent the percentage of mosquitoes trapped in the respective upwind chamber. Black bars represent the pure finger, white bars the mixture of finger plus the odor stimulus indicated below the bar; stimulus labels as described in FIG. 3A; asterisks indicate a significant preference ($P<0.05$, t-test for paired samples).

The results demonstrate that when adding a certain compound, the scent of the human body of some persons may become more attractive to the mosquitoes (e.g. FIG. 4 C, capronic acid in all concentrations). It is equally possible that addition of a compound, especially when used in a high concentration, makes the scent less attractive (FIG. 4 A, Ammonia+100). This effect depends upon the person involved. However, addition of acetic acid scent in an up to 50-fold higher concentration than that of the standard blend did not change the attractiveness with any of the persons involved.

EXAMPLE 5

The apparatus used for the above-described tests is shown in FIG. 5. The Figure shows the experimental device, wherein A) is a top view of the olfactometer for testing mosquitoes' odour preference. The spatial distribution of odourants in the air are outlined according to the appearance of $TiCl_4$ smoke, which was injected into the olfactometer instead of the odour stimulus. In the arms of the olfactometer the smoke was homogeneous distributed[20]. More turbulent odour eddies and filaments emerged in the rectangular chamber, although a steep gradient between both air streams can still be observed in the joined straight tube. For each test, 20 female *A. aegypti* mosquitoes were used from cultures of Bayer AG in Monheim, 5-15 days old, which had no blood meal before. Details of the olfactometer and the experimental procedure are described elsewhere (Geier, M. & Boeckh, J. *Entomol. exp. appl.* 92, 9-19 (1999); Geier, M., Bosch, O. J. & Boeckh, J. *Chem. Sens.* 24, 647-653 (1999)).

At stimulus onset, 20 mosquitoes in the start chamber are set free to fly through the olfactometer. During their zig zag flight through the straight tube they encounter alternately air streams from either arm. Following the favoured air stream during upwind flight the mosquitoes enter the respective upwind chamber where they are counted 30 s after stimulus onset. The percentage of mosquitoes found in each chamber serves as the measure for attractiveness of the odour stimulus. Odour stimuli were produced by passing purified air through Erlenmeyer flasks which contain the odour solution (Geier, M., Bosch, O. J. & Boeckh, J. *Chem. Sens.* 24, 647-653 (1999); Geier, M., Bosch, O. J. & Boeckh, J. *J. exp. Biol.* 202, 1639-1648 (1999)). The odour laden air is injected into the air stream of the olfactometer.

B) shows that by varying the concentration of the compound in the Erlenmeyer flask or the flow rate of the passing air a wide range of odour concentrations can be produced. Table 1 summarises the tested compounds and how the different stimulus doses were produced. Instead of synthetic odourants also a human hand can be placed in the air stream of the olfactometer to test the natural blend of skin odourants.

The following table summarises the compounds used in the experiments described above and gives the concentration used in the different experiments. The values listed in the column labelled "concentration" refer to the concentration of the odorant in the erlenmeyer flask that is part of the device as shown in FIG. 5 and explained in example 5. The concentration achieved in the air stream will depend upon the air flow. The air flow rates used are given in the table, however, when a differently dimensioned apparatus is used, different air flows may be used. The concentration of the compounds in the airstream may easily be measured by methods known to the person of skill in the art. They may be derived by calculation from the starting amount of a substance, the amount left in the erlenmeyer flask after a given time, and the air stream that has flowed through the flask and through the main tube during said time.

TABLE 1

Tested odourants

| Component | Stimulus label[a] | Concentration[b] | Solvent | Flow rate[c] [ml/min] | Stimulus dose[d] [µmol/min] |
|---|---|---|---|---|---|
| L-lactic acid | $LA_{-30}$ | Pure | Water | 2 | 0.002 (Geier et. al., 1999a) |
| | $LA_{-10}$ | Pure | | 5 | 0.005 |
| | $LA_{-5}$ | Pure | | 10 | 0.01 |
| | $LA_{-2}$ | Pure | | 20 | 0.02 |
| | $LA_{ST}$ | Pure | | 50 | 0.05 |
| | $LA_{+3}$ | Pure | | 150 | 0.15 |
| | $LA_{+5}$ | Pure | | 250 | 0.25 |
| | $LA_{+20}$ | Pure | | 1000 | 1.0 |
| Caproic acid | $CA_{-30}$ | 1% | Paraffin | 3 | 0.001 (Kafka, 1970) |
| | $CA_{-5}$ | Pure | | 1 | 0.006 |
| | $CA_{St}$ | Pure | | 5 | 0.03 |
| | $CA_{+5}$ | Pure | | 25 | 0.15 |
| | $CA_{+20}$ | Pure | | 100 | 0.6 |
| Ammonia | $AM_{-30}$ | 0.025% | Water | 0.3 | 0.003 (Geier, 1999b) |
| | $AM_{-5}$ | 0.025% | | 2 | 0.02 |
| | $AM_{St}$ | 0.25% | | 1 | 0.09 |
| | $AM_{+5}$ | 0.25% | | 5 | 0.45 |
| | $AM_{+10}$ | 0.25% | | 10 | 0.9 |
| | $AM_{+30}$ | 0.25% | | 30 | 2.65 |
| | $AM_{+100}$ | 0.25% | | 100 | 9 |
| | $AM_{+300}$ | 0.25% | | 300 | 26.5 |
| Acetic acid | $AC_{-30}$ | 0.0001% | Paraffin | 3 | 0.0007 (Kafka, 1970) |
| | $AC_{-5}$ | 0.001% | | 2 | 0.004 |
| | $AC_{St}$ | 0.01% | | 2 | 0.02 |
| | $AC_5$ | 0.01% | | 10 | 0.1 |
| | $AC_{25}$ | 0.01% | | 50 | 0.4 |
| | $AC_{50}$ | 0.01% | | 100 | 0.8 |
| Control (no substance added) | Co | pure | paraffin | 300 | — |
| | | pure | water | 300 | — |

EXAMPLE 6

Herein we investigate if heptanoic acid can replace caproic acid in the attractive mixture.

Olfactometer and Methods

See Example 1, FIG. 5. and table 1.

Results

The behavioural responses of the mosquitoes are summarized in table 2. The responses to the blends containing heptanoic acid did not differ significantly from the blend with caproic acid and there was no significant difference between the two concentrations (Attraction: ANOVA, p=0.257, F=1.382; Activation: ANOVA, p=0.490, F=0.720). The results clearly show that heptanoic acid can be used instead of caproic-acid in the synthetic mixture.

TABLE 2

Behavioural responses of *Ae. aegypti*

| | | Test chamber | | Control chamber | | | Active | |
|---|---|---|---|---|---|---|---|---|
| n | Stimulus | % T[1] | S.E. | Stimulus | % C[2] | S.E. | % A[3] | S.E |
| 16 | Mix | 81[b] | 3.2* | No | 0.2 | 0.3 | 89[b] | 2.2 |
| 16 | Mix with Oe low | 76[b] | 2.9* | No | 0.1 | 0.4 | 93[b] | 1.4 |
| 16 | Mix with Oe high | 85[b] | 1.2* | No | 0.2 | 0.8 | 91[b] | 1.9 |

Means from n tests per treatment; each test with 18-22 mosquitoes. [1]Mean percentage of mosquitoes trapped in the test chamber, [2]mean percentage of mosquitoes trapped in the control chamber, [3]mean percentage of mosquitoes which left the release chamber. *significant difference (P < 0.01) of mean percentage in test- and control chamber: t-test for paired samples. Within all experiments means in the test- or active columns followed by the same letter are not significantly different (P < 0.05, one-way ANOVA: LSD post hoc test).
Abbreviations:
Mix = lactic acid 1.5 ml/min flow rate, ammonia 0.1 ml/min, caproic acid 0.5 ml/min; Mix with Oe low = lactic acid 1.5 ml/min, ammonia 0.1 ml/min, heptanoic acid 0.5 ml/min; Mix with Oe high = lactic acid 1.5 ml/min, ammonia 0.1 ml/min, heptanoic acid 3 ml/min.

EXAMPLE 7

In this example we show the attractive effect of our blend composition in laboratory room tests with an ventilator insect trap that sucks in the flying insects. We also investigated the attractiveness of our blend compositions to different mosquito species. The results presented in table 3 show that the blend clearly enhances the effectiveness of the trap. A mixing ratio near to the optimum blend catches is almost as attractive as a human test person. Mixing ratios which are very different to the optimum blend are less attractive. This holds true for all tested species.

TABLE 3

Release and recapture of mosquitoes in a laboratory room using an insect ventilator trap Mean trapped after 20 min

| Treatment | n | Culex quinquefasciatus | Anopheles stephensi | Aedes aegypti | Aedes albopictus |
|---|---|---|---|---|---|
| No attractants | 6 | 1.0 | 0.1 | 2.3 | 1.2 |
| Blend A | 6 | 6.7 | 5.8 | 8.2 | 6.4 |
| Blend B | 6 | 2.3 | 1.9 | 1.2 | 0.3 |
| Blend C | 6 | 3.2 | 2.6 | 4.1 | 2.9 |
| Person K | 4 | 7.0[1] | 6.2 | 9.6 | 8.3 |

Released 10-14 female mosquitoes per test, 4-14 days old, no blood meal prior to release
[1] = number of mosquitoes landed on test person
n = number of performed tests
Blend A: Mixing ratio of lactic acid, caproic acid and ammonia: 1:2:0.3
Vial 1: evaporation rate of lactic acid: 0.02 mmol/h
Vial 2: evaporation rate of caproic acid: 0.04 mmol/h
Vial 3: evaporation rate of ammonia: 0.006 mmol/h
Blend B: Mixing ratio of lactic acid, caproic acid and ammonia: 1:2:80
Vial 1: evaporation rate of lactic acid: 0.02 mmol/h
Vial 2: evaporation rate of caproic acid: 0.04 mmol/h
Vial 3: evaporation rate of ammonia: 1.6 mmol/h
Blend C: Mixing ratio of lactic acid, caproic acid and ammonia: 1:200:0.3
Vial 1: evaporation rate of lactic acid: 0.02 mmol/h
Vial 2: evaporation rate of caproic acid: 4.0 mmol/h
Vial 3: evaporation rate of ammonia: 0.006 mmol/h In all experiments the volatiles were applied in different vials filled with the pure test compounds; each compound was filled in a separated vial. Using different sizes of the openings of the vials, different release rates could be produced. The released amount of each compound was estimated by weight loss data. The compounds were mixed in the gaseous phase using a ventilator.

EXAMPLE 8

In this example we show the data of our field experiments in Brazil using the same insect trap as in example 7. Using the optimum mixing ratio our attractants caught mosquitoes which were present in this area in high numbers compared to a trap without attractants. Surprisingly we also caught *Drosophila* sp. in relative high numbers with our optimum blend. This shows that our blend composition is also attractive for *Drosophila* flies.

Trapping of free flying insects in a domestic environment in Belo Horizonte/Brazil during 5 days.

| | Traps with different lures | | | |
|---|---|---|---|---|
| Species | No attractants | Blend A | Blend B | Human landing rate |
| *Drosophila* sp. | 0.2 | 31.4 | 10.4 | 0 |
| *Aedes aegypti* | 2.0 | 42.8 | 13.9 | 56.4 |
| *Culex* sp. | 0.7 | 21.1 | 7.2 | 30.3 |
| *Plebotomus* sp. | 0 | 1.2 | 2.5 | 0.8 |

Trapped insects/24 h
Blend A: Mixing ratio of lactic acid, caproic acid and ammonia: 1:2:0.3
Vial 1: evaporation rate of lactic acid: 0.02 mmol/h
Vial 2: evaporation rate of caproic acid: 0.04 mmol/h
Vial 3: evaporation rate of ammonia: 0.006 mmol/h
Blend B: Mixing ratio of lactic acid, caproic acid and ammonia 1:520:0.3
Vial 1: evaporation rate of Lactic acid: 0.02 mmol/h
Vial 2: evaporation rate of caproic acid: 10.4 mmol/h
Vial 3: evaporation rate of ammonia: 0.006

The distance between each trap was at least 4 m. Each day the position of the traps was changed randomly.

In all experiments the volatiles were applied in different vials filled with the pure test compounds; each compound was filled in a separated vial. Using different sizes of the openings of the vials, different release rates could be produced. The released amount of each compound was estimated by weight loss data. The compounds were mixed in the gaseous phase using a ventilator.

Listing of the dosages of the tested compounds. Stock solutions for preparing the odour sources were ammonium hydroxide (17093, 25%, Fluka, Buchs), lactic acid (100366, 90%, Merck, Darmstadt), acetic acid (45731, 99.8%, Fluka, Buchs), and caproic acid (21529, 99.5%, Fluka, Buchs).

[a] Stimulus labels refer to the marking of stimuli in figures and text. Starting from the standard doses labelled with $_{ST}$ the numbers of the stimuli labels indicate increasing or decreasing doses compared to the standard. For example $AM_{-5}$ means a fivefold less dose than $AM_{ST}$, $AM_{+30}$ a thirtyfold higher dose than $AM_{ST}$.

[b] Concentration (% per vol.) of stimulus solution in Erlenmeyer flask. Solvents were distilled water or paraffin (Uvasol®, 107161, Merck, Darmstadt).

[c] Flow rate of charcoal filtered air passed through the flask.

[d] Output of test component injected into the olfactometer as calculated from calibrations of quoted authors. For acetic acid the doses were extrapolated from Kafka's (1970) calibration data of butyric- and caproic acid. See also FIG. 1 for description of odour presentation.

The invention claimed is:

1. A composition for attracting mosquitoes, which consists essentially of:
   (a) lactic acid or an acceptable salt thereof;
   (b) caproic acid or an acceptable salt thereof; and
   (c) ammonia,
in a respective molar ratio of 5:3:9.

2. A method of attracting mosquitoes at a level of attractiveness equivalent to a level of attractiveness of a human body comprising the step of exposing an environment with an evaporated composition consisting essentially of
   (a) lactic acid or an acceptable salt thereof;
   (b) caproic acid or an acceptable salt thereof; and
   (c) ammonia,
in a respective molar ratio of 5:3:9 which composition is effective to attract mosquitoes.

3. The method of attracting mosquitoes defined in claim 2 further comprising the step of trapping the attracted mosquitoes.

4. A composition for attracting mosquitoes or fruit flies, which consists essentially of:
 (a) lactic acid or an acceptable salt thereof;
 (b) caproic acid or an acceptable salt thereof; and
 (c) ammonia,
in a respective molar ratio of 1:2:0.3.

5. A method of attracting mosquitoes or fruit flies comprising the step of exposing an environment with the composition defined in claim 4 in an amount effective to attract mosquitoes or fruit flies.

* * * * *